United States Patent [19]

Ishida et al.

[11] Patent Number: 5,786,386
[45] Date of Patent: Jul. 28, 1998

[54] ANTIBACTERIAL AND FUNGICIDAL AGENT

[75] Inventors: Kenya Ishida; Kazutoshi Sakurai, both of Hiratsuka, Japan

[73] Assignee: Takasago International Corporation, Tokyo, Japan

[21] Appl. No.: 678,598

[22] Filed: Jul. 15, 1996

[30] Foreign Application Priority Data

Jul. 18, 1995  [JP]  Japan .................................. 7-181656

[51] Int. Cl.$^6$ .......................... A01N 33/04; A01N 43/30; A01N 43/50
[52] U.S. Cl. .......................... 514/466; 514/400; 514/655
[58] Field of Search .................................. 514/466, 655, 514/400; 548/335.5; 549/440; 564/389, 390, 391, 384

[56] References Cited

U.S. PATENT DOCUMENTS 4,372,969  2/1983  Lafon .................................... 424/282

FOREIGN PATENT DOCUMENTS 62-234004  10/1987  Japan .
63-2904  1/1988  Japan .

OTHER PUBLICATIONS

Biochemical Pharmacology, vol. 30, No. 22, pp. 3045–3049, 1981, Robin J. Breckenridge, et al., "Inhibition of Neuronal GABA Uptake and Glial β–Alanine Uptake by Synthetic GABA Analogues".

Biochemical Pharmacology, vol. 34, No. 23, pp. 4173–4177, 1985, "Non–Selective Inhibition of GABA and 5–HT Uptake Systems in Rat Brain by N–n–Alkyl Hydroxybenzylamine and N–n–alkyl Phenylethylamine Derivatives".

J. Med. Chem., vol. 36, No. 9, pp. 1262–1271, 1993, Melvin J. Yu, et al., "Benzylamine Antioxidants: Relationship Between Structure, Peroxyl Radical Scavenging, Lipid Peroxidation Inhibition, and Cytoprotection".

Journal of Neurochemistry, vol. 37, No. 4, pp. 837–844, 1981, Robin J. Breckenridge, et al., "Inhibition of [$^3$H] GABA Binding to Postsynaptic Receptors in Human Cerebellar Synaptic Membranes by Carboxyl and Amino Derivatives of GABA ".

Primary Examiner—Richard L. Raymond
Attorney, Agent, or Firm—Oblon, Spivak, McClelland, Maier & Neustadt, P.C.

[57] ABSTRACT

The present invention provides an antibacterial and fungicidal agent containing an amino compound of formula (1) or a salt thereof. The invention also provides a method for imparting antibacterial and fungicidal properties to a variety of objects using the compound.

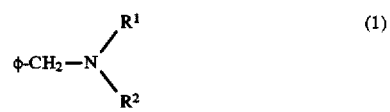

wherein φ represents a phenyl group, a substituted phenyl group (wherein the substituents are 1-5 members arbitrarily selected from the group consisting of a hydroxyl group, halogen atoms, lower alkoxyl groups, trifluoromethyl group, an amino group, and a methylenedioxy group), or an imidazolyl group; $R^1$ represents a hydrogen atom or a lower alkyl group; and $R^2$ represents a C6–C12 alkyl group. The amino compound of formula (1) or a salt thereof exhibits excellent antibacterial effects and fungicidal effects, and when it is applied to a variety of articles used in industry, commodities, etc., enhanced antibacterial effects and fungicidal effects are obtained.

9 Claims, No Drawings

ANTIBACTERIAL AND FUNGICIDAL AGENT

BACKGROUND OF THE INVENTION

1. Field of the Invention

The present invention relates to antibacterial and fungicidal agents which are used to impart antibacterial or bactericidal properties to commodities and a variety of articles used in industry.

2. Related Art

Hitherto, a number of antibacterial substances have been used or proposed to be used to impart antibacterial and fungicidal properties to commodities including cosmetics, toiletry goods, sterilizing agents, deodorants, and detergents, and to a variety of articles used in industry including paints, wallpapers, adhesives, wallboards, tiles, cement, concrete, molded resins (plastics, etc.), fibers (clothes, etc.) and porcelains (tableware). Among such antibacterial substances, a wide variety of organic compounds such as organic nitrogen-containing substances, organic sulfur-containing substances, organic tin-containing substances, organic phosphorus-containing substances, and organic chlorine-containing substances have been used according to the characteristics or intended use of articles or materials. However, many of these compounds have drawbacks; they have relatively strong toxicity which cannot be neglected from the viewpoint of safety, their effects are easily lost within short periods of time, and they allow resistant bacteria to emerge with ease.

Meanwhile, some of the amino compounds represented by the below-described formula (1) or their salts, which are active components of the antibacterial and fungicidal agents of the present invention have already been described in Japanese Patent Applications Laid-Open (kokai) Nos. 62-234004 and 63-2904, etc. as injurious insect repellents and plant growth regulators. Some of the others have been reported to exhibit pharmaceutical activities such as GABA (gamma aminobutyric acid) inhibiting activities related to the central nervous transmission system (Biochemical Pharmacology, Vol. 34, No. 23, p4173–4177 (1985)) or inhibitory activities against the formation of lipid peroxides (Journal of Medicinal Chemistry, Vol. 36, No. 9, p1262–1271 (1993)). However, these publications do not contain any description suggesting that the amino compounds of formula (1) or their salts exhibit antibacterial or fungicidal activities, or that they are or can be used as antibacterial agents or fungicidal agents.

Compounds which are used for the purpose of treating the aforementioned commodities and articles used in industry are desired to have wide antibacterial spectra. Moreover, they are generally expected to have a high level of stability against humidity and temperature, and to exhibit excellent antibacterial activities even when they are used in small amounts. Furthermore, it is desired that these compounds per se exhibit a high level of safety for protecting not only human bodies but also the environment.

SUMMARY OF THE INVENTION

The present inventors conducted careful studies regarding the use of amino compounds of formula (1) and their salts and found that these compounds exhibit excellent antibacterial activities against various bacteria including gram-positive bacteria such as *Bacillus subtilis*, *Staphylococcus aureus*, *Staphylococcus epiderumidis*, and *Corynebacterium minutissium*; gram-negative bacteria such as *Pseudomonas aeruginosa*; and hyphomycetes such as *Aspergillus niger* and *Candida tropicalis*. The inventors also found that the compounds are very safe, causing reduced skin irritation and exhibiting minimized sensitization. The present invention was accomplished based on these findings.

Accordingly, an object of the present invention is to provide antibacterial and fungicidal agents which exhibit excellent antibacterial activities, which are very safe, and which are effectively used to provide commodities and articles used in industry with antibacterial and fungicidal properties.

In one aspect of the present invention, there is provided an antibacterial and fungicidal agent comprising an amino compound represented by the following formula (1) or a salt thereof:

(1)

wherein $\phi$ represents a phenyl group, a substituted phenyl group (wherein the number of substituents is 1 from 5 inclusive, and the substituents, which may be identical to or different from one another, are selected from the group consisting of a hydroxyl group, halogen atoms, lower alkoxyl groups, trifluoromethyl group, an amino group, and a methylenedioxy group), or an imidazolyl group; $R^1$ represents a hydrogen atom or a lower alkyl group; and $R^2$ represents a C6–C12 alkyl group.

In another aspect of the present invention, there is provided an antibacterial and fungicidal composition comprising the amino compound of formula (1) or a salt thereof and a carrier therefor.

In a further aspect of the present invention, there is provided a method for imparting antibacterial and fungicidal properties to objects which may allow propagation of bacteria or fungi, via adding to the objects an amino compound of formula (1) or a salt thereof or via treating the objects with an amino compound of formula (1) or a salt thereof.

The above and other objects, features, and advantages of the present invention will become apparent from the following description.

DESCRIPTION OF PREFERRED EMBODIMENTS

Objects to which the antibacterial and fungicidal agents of the present invention may be applied include anything in which bacteria or fungi and generated. Examples of such objects include articles used in industry such as paints, wallpapers, adhesives, wallboards, tiles, cement, concrete, resin molds (plastics, etc.), fibers (clothes, etc.), and porcelains (tableware, etc.); and commodities such as cosmetics, toiletry articles, sterilizers, deodorants, and detergents.

In formula (1), examples of lower alkoxyl groups which serve as substituents of the substituted phenyl group $\phi$ include C1–C4 linear or branched alkoxyl groups such as methoxyl, ethoxyl, n-propoxyl, isopropoxyl, n-butoxyl, isobutoxyl, sec-butoxyl, and tert-butoxyl; examples of halogen atoms include fluorine, chlorine, bromine, and iodine; and examples of imidazolyl groups represented by $\phi$ include 2-imidazolyl. Examples of lower alkyl groups represented by $R^1$ include C1–C4 linear or branched alkyl groups such as methyl, ethyl, n-propyl, isopropyl, n-butyl, isobutyl, sec-butyl, and tert-butyl. C6–C12 alkyl groups represented by $R^2$ may be linear or branched, and examples thereof include hexyl, octyl, decyl, dodecyl (lauryl).

The amino compounds represented by formula (1) and their salts may be prepared through known methods. For example, compounds of formula (1) wherein $R^1$ is hydrogen may be prepared via any one of the following reaction schemes A, B, or C, whereas compounds of formula (1) wherein $R^1$ is lower alkyl may be prepared through N-alkylation of compounds resulting from any one reaction schemes A, B, or C, i.e., compounds of formula (1) wherein $R^1$ is hydrogen. N-alkylation may be performed in a way similar to that described in reaction scheme C. The symbols $\phi$ and $R^2$ appearing in the below-described reaction schemes have the same meanings as defined hereinbefore. X represents a halogen atom.

Reaction Scheme A

Aromatic aldehyde (2) is reacted with alkyl amine (3) for 0.5–6 hours at 5°–30° C. in the presence of an organic solvent such as ethyl acetate, ethanol, or tetrahydrofuran, thereby obtaining compound (4). Subsequently, compound (4) thus obtained is subjected to hydrogenation in situ in the presence of a catalyst such as 5% Pd-C or Raney nickel (hydrogen pressure: 3–20 kg/cm$^2$), thereby obtaining compound (1a) of formula (1) in which $R^1$ is hydrogen.

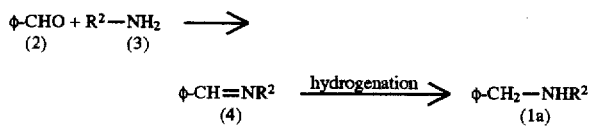

Reaction Scheme B

Aromatic aldehyde (2) is reacted with alkyl amine (3) for 0.5–6 hours at 0°–50° C., preferably 15°–25° C., in the presence of ether-acetic acid, ethanol, or sodium acetate. Subsequently, a reducing agent such as a pyridine-borane complex, sodium borohydride, or lithium aluminum hydride is added to obtain compound (1a) of formula (1) in which $R^1$ is hydrogen.

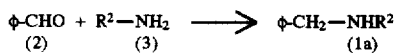

Reaction Scheme C

Aromatic alkyl amine (5) is reacted with alkyl halide (6) for 2–24 hours at 30°–110° C. in the presence of an organic solvent such as chloroform, toluene, or dimethylformamide, so as to remove hydrogen halide. As a result, compound (1a) of formula (1) in which $R^1$ is hydrogen is obtained.

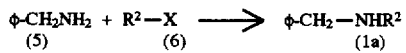

In each of the above reaction schemes A, B, and C, the starting materials, i.e., aromatic aldehyde (2) and aromatic alkyl amine (5), may be commercial compounds having substituents corresponding to amino compounds (1). These commercial compounds may be used after they are suitably formulated. Alternatively, they may be used as they are.

The amino compounds of formula (1) synthesized through the above-described reaction scheme A, B, or C may be converted into a variety of salts using routine methods. Examples of such salts include, but are not limited to, salts of any one of the amino compounds and inorganic acid such as hydrochloric acid or phosphoric acid, and salts of any one of the amino compounds and organic acid such as fumaric acid, maleic acid, citric acid, or tartaric acid.

The amino compounds of formula (1) or their salts produced via the above reaction scheme A, B, or C may be separated and purified using conventional separation or purification procedures such as extraction, concentration, neutralization, distillation, recrystallization, column chromatography, thin layer chromatography, etc.

Specific examples of the amino compounds of formula (1) or their salts obtained through reaction the above-described scheme A, B, or C are shown in Table 1.

TABLE 1

| | In formula (1) | | |
|---|---|---|---|
| Compound No. | R1 | R2 | $\phi$ |
| 1 | H | $C_{12}H_{25}$ | 3,4-Methylenedioxyphenyl |
| 2 | H | $C_6H_{13}$ | 3,4-Methylenedioxyphenyl |
| 3 | H | $C_{12}H_{25}$ | 3-Hydroxyphenyl |
| 4 | H | $C_{12}H_{25}$ | 4-Aminophenyl |
| 5 | H | $C_{10}H_{21}$ | 2-Methoxyphenyl |
| 6 | H | $C_{12}H_{25}$ | 4-Methoxyphenyl |
| 7 | H | $C_{12}H_{25}$ | 2,4-Difluorophenyl |
| 8 | H | $C_{12}H_{25}$ | 4-Hydroxy-3-Methoxyphenyl |
| 9 | H | $C_{12}H_{25}$ | 3,4-Dimethoxyphenyl |
| 10 | H | $C_{12}H_{25}$ | 3-Hydroxy-4-Methoxyphenyl |
| 11 (Oxalate) | H | $C_{12}H_{25}$ | 2,3-Dihydroxyphenyl |
| 12 | H | $C_{12}H_{25}$ | 2,4-Dichlorophenyl |
| 13 | H | $C_{12}H_{25}$ | 4-Trifluoromethylphenyl |
| 14 | $CH_3$ | $C_{12}H_{25}$ | 2,4,5-Trimethoxyphenyl |
| 15 (Dihydrochloride) | H | $C_{12}H_{25}$ | 2-Imidazolyl |

The amino compounds of formula (1) or salts thereof may be applied, singly or in combination of two or more, irrespective of the form, i.e., solid, powder, or liquid, to objects which are desired to be provided with antibacterial properties or fungicidal properties, i.e., aforementioned articles used in industry or commodities.

In use, the amino compounds of formula (1) or salts thereof may be directly applied. Alternatively, these compounds may be used as antibacterial and fungicidal compositions after the compounds are combined with a suitable carrier. Carriers which may be used for this purpose include, but are not limited to, gases (e.g., propellants), liquids (solvents), and solids (powder, sheets, polymers, etc.).

Objects which may allow propagation of bacteria or fungi therein may be provided with antibacterial properties and bactericidal properties by adding or incorporating the amino compounds of formula (1) or salts thereof to these objects. Alternatively, these objects may be treated with amino compounds of formula (1) or salts thereof.

Specifically, amino compounds of formula (1) or salts thereof may be directly kneaded along with the compositions of the target articles. Alternatively, a suitable amount of nontoxic base material may be added to amino compounds of formula (1) or salts thereof if needed, and the resultant mixtures may then be formed into liquids or aerosols. In use, the liquids or aerosols may be blended with target articles which require antibacterial and fungicidal treatment, or may be vaporized and applied to these articles. Base materials which may be used for this purpose are not particularly limited. Specifically, organic solvents (such as ethanol, propylene glycol, and glycerol) may be used. When the amino compounds of formula (1) or salts thereof are to be applied to sheet-like materials such as paper, cloths, or non-woven fabrics, these materials may be directly soaked with these compounds.

The range and manner of application of amino compounds of formula (1) and their salts are suitably changed in accordance with the kinds, materials used, purpose of use, etc. Usually, they are preferably used in amounts of approximately 0.0001–2% by weight, particularly 0.001–1% by weight based on the weight of the total composition of the product.

Target substances or articles to be treated so as to have antibacterial and fungicidal properties according to the present invention may contain optional components which are suitable to their respective purpose of use. For example, when cosmetics are concerned, the following agents may also be incorporated if needed in a conventional manner: hydrophobic bases such as Vaseline, squalane, and beeswax; hydrophilic bases such as propylene glycol; alcohols such as ethyl alcohol; emulsifiers such as fatty acid monoglycerides, sorbitan fatty acid esters; polyoxyethylene alkyl ethers; pigments; perfumes; and other ingredients such as nutrients, humectants, UV absorbers, etc. Similarly, products other than cosmetics may also incorporate a variety of ingredients in accordance with the characteristics of materials used, kinds, etc. of the products.

Additionally, the antibacterial and fungicidal agents according to the present invention may be used optionally in combination with other antibacterial and fungicidal agents which are suitable to purpose of use, if needed. For example, such optionally-combined agents include organic substances such as organic nitrogen-containing substances and organic sulfur-containing substances, and inorganic substance such as silver, zinc and copper.

EXAMPLES

The present invention will next be described in detail by referential examples and examples of invention (applications in various products). However, these referential examples and examples of the invention should not be construed as limiting the invention.

Referential Example 1 (Reaction scheme A; Synthesis of compound No. 15)

In a 500-ml autoclave were placed 2-imidazolecarboxaldehyde (6.9 g (70 mmol), product of Aldrich), n-laurylamine (12.8 g (69 mmol)), 5% Pd-C (2 g), and ethyl acetate (200 ml). The contents of the flask were stirred for 24 hours at room temperature under hydrogen (20 kg/cm$^2$). The catalyst was removed, and the solvent was concentrated. Purification via silica gel column chromatography (n-hexane:ethyl acetate=2:1) afforded 11.0 g of N-lauryl-2-imidazole methyl amine as white crystals (yield: 60%).

$^1$H-NMR δ(ppm) (CDCl$_3$);
0.9(3H, t), 1.2–1.3(18H, m), 1.4–1.5(2H, m), 2.6–2.7(2H, t), 3.9(2H, s), 7.0(2H, s)

MS; 265(M$^+$)

A portion of the obtained while crystals (1.0g (3.8 mmol)) was dissolved in 12.5% HCl-ethanol (10 ml), and the solution was stirred for 1 hour at 30° C. After stirring, ethanol was evaporated under reduced pressure (20 mmHg, 50° C.), and the residue was dried (2.0 mmHg, 50° C., 2 hours), thereby obtaining 1.08 g of a dihydrochloric acid salt of N-lauryl-2-imidazole methyl amine as white crystals (yield: 100%).

Referential Example 2 (Reaction scheme B; Synthesis of compound No. 10)

In a 100-ml round-bottomed flask were placed n-laurylamine (11.1 g (60 mmol)) and isovaniline (1.52 g (10 mmol)) under nitrogen. While stirring, diisopropylether (17.5 ml) and glacial acetic acid (5 ml) were sequentially added dropwise. After completion of addition, the mixture was stirred for approximately 2 hours at room temperature, followed by the addition of a borane-pyridine complex (1.2 ml (10 mmol), product of Aldrich) over 10 minutes. The mixture was stirred for a further 2 hours. Subsequently, 5N-HCl (12 ml) was added dropwise and the resultant mixture was stirred for 10 minutes. The pH of the mixture was turned to basic using an aqueous 5N—NaOH solution. The product formed was extracted using diisopropyl ether, concentrated, and purified via silica gel column chromatography n-hexane:ethyl acetate=2:1), thereby obtaining 2.6 g of N-lauryl-3-hydroxy-4-methoxybenzylamine as mud yellow crystals (yield: 82%).

$^1$H-NMR δ(ppm) (CDCl$_3$);
0.9(3H, t), 1.2–1.3(18H, m), 1.4–1.5 (2H, m), 2.6(2H, t), 3.5(1H, s), 3.7(2H, s), 3.9(3H, s), 6.8(2H, s), 6.9(1H, s)

MS; 321 (M$^+$)

Referential Example 3 (Reaction scheme C; Synthesis of compound No. 12)

In a 100-ml round-bottomed flask were placed 2,4-dichlorobenzylamine (3.5 g (20 mmol)), triethylamine (4.0 g (40 mmol)), and chloroform (10 ml) under nitrogen. While stirring, laurylbromide (4.9 g (20 mmol)) in chloroform (5 ml) was added dropwise at 50°–60° C. The mixture was stirred for 6 hours. The reaction mixture was cooled to room temperature and concentrated. The resultant concentrate was dissolved in ethyl acetate, washed with water, and purified via silica gel column chromatography (chloroform:methanol=10:1), thereby obtaining 2.3 g of N-lauryl-2,4-dichlorobenzylamine as pale yellow crystals (yield: 34%).

$^1$H-NMR δ(ppm) (CDCl$_3$);
0.87(3H, t), 1.2–1.3 (18H, m), 1.8–1.9(2H, m), 2.8–2.9(2H, m), 4.2(2H, s), 7.4–7.45(1H, m), 7. 5(1H, m), 7.85(1H, d)

MS; 344(M$^+$)

A portion of the thus obtained pale yellow crystals (1.0 g (2.9 mmol)) was dissolved in 12.5% HCl-ethanol (10 ml), and the solution was stirred for 1 hour at 30° C. After stirring, ethanol was evaporated under reduced pressure (20 mmHg, 50° C.), and the residue was dried (2.0 mmHg, 50° C., 2 hours), thereby obtaining 1.07 g of a hydrochloric acid salt of N-lauryl-2,4-dichlorobenzylamine as yellowish white crystals (yield: 100%).

Example 1 (Cream)

The below-listed components were mixed in accordance with a conventional method, thereby preparing a cream (100 g).

| Components | Proportion (% by weight) |
| --- | --- |
| Compound No. 1 | 0.005 |
| Beeswax | 10.0 |
| Solid paraffin | 5.0 |
| Vaseline | 15.5 |
| Liquid paraffin | 39.0 |
| Sorbitan sesquioleate | 3.5 |
| Perfume | 0.5 |
| Purified water | balance |

Example 2 (Lotion)

The below-listed components were mixed in accordance with a conventional method, thereby preparing a lotion (100 g).

| Components | Proportion (% by weight) |
| --- | --- |
| Compound No. 10 | 0.005 |
| Glycerol | 2.0 |
| 1,3-Butylene glycol | 2.0 |
| Sodium citrate | 0.1 |
| Ethanol | 15.0 |
| Polyethylene oleyl ether | 0.5 |
| Purified water | balance |

Example 3 (Shampoo)

The below-listed components were mixed in accordance with a conventional method, thereby preparing a shampoo composition (100 g).

| Components | Proportion (% by weight) |
| --- | --- |
| Compound No. 1 | 0.005 |
| Decanoic acid | 0.05 |
| Triethanolamine laurylsulfate | 18.5 |
| Hydroxypropylmethylcellulose | 15.0 |
| Ammonium laurylsulfate | 8.0 |
| Cocamide | 4.0 |
| Palmitic acid | 0.3 |
| 1,3-Dimethylol-5,5-dimethyl hydantoin | 0.15 |
| Disodium ethylenediamine-tetraacetate | 0.05 |
| Citric acid | small amount |
| Sodium chloride | small amount |
| Perfume | 0.85 |
| Purified water | balance |

Example 4 (Detergent)

The below-listed components were mixed in accordance with a conventional method, thereby preparing a detergent (100 g).

| Components | Proportion (% by weight) |
| --- | --- |
| Compound No. 14 | 0.005 |
| Senesionic acid | 0.1 |
| White Vaseline | 6.0 |
| Alkylallylpolyether sulfonate | 50.0 |
| Cholesterol | 2.0 |
| Purified water | balance |

Example 5 (Paint)

The below-listed components were mixed in accordance with a conventional method, thereby preparing an antibacterial and fungicidal paint.

| Components | Proportion (% by weight) |
| --- | --- |
| Compound No. 1 | 0.002 |
| Red iron oxide | 10.0 |
| Talc | 20.0 |
| Zinc oxide | 20.0 |
| Rubber chloride | 12.0 |
| Plasticizer | 2.0 |
| Xylene | 31.0 |

Example 6 (Cement)

The below-listed components were used to obtain a cement composition.

| Components | Proportion (% by weight) |
| --- | --- |
| Compound No. 10 | 0.5 |
| Ordinary portland cement | 26.5 |
| River sand | 55.0 |
| Water | 18.0 |

Example 7 (Calking agent)

The below-listed components were used to obtain a calking agent.

| Components | Proportion (% by weight) |
| --- | --- |
| Compound No. 14 | 0.2 |
| Polypropylene resin | 99.8 |

Test Examples

Antibacterial effect, antibacterial activities, and safety of amino compounds of formula (1) and salts thereof were tested.

Test Example 1 (antibacterial effect)

Method

Each of the cream obtained in Example 1 and a cream prepared in a manner similar to that described in Example 1 excepting that compound 1 was not contained (comparative product) was applied onto a piece of cloth having a size of 5×5 cm. Each piece of cloth was affixed onto a potato dextrose agar medium and cultured for 30 days. Growth of bacteria was observed.

Results

In the piece of cloth to which the cream of the present invention containing compound No. 1 was applied, growth of bacteria was never observed. In the piece of cloth to which the comparative product was applied, growth of bacteria was observed after 2–3 days from the application.

Test Example 2 (antibacterial activities)

Using the below-listed species of bacteria, antibacterial activities of amino compounds were investigated. Butyl paraben was used as a control compound.

Gram-positive bacteria:
   *Bacillus subtilis* IFO 3009 (Bs.),
   *Staphylococcus aureus* IAM 1011 (Sa.),
   *Staphylococcus epidermidis* (Se.), and
   *Corynebacterium minutissium* ATCC 23348 (Cm.)

Gram-negative bacteria:
   *Pseudomonas aeruginosa* IFO 13275 (Pa.)

Hyphomycetes:
   *Aspergillus niger* IAM 2534 (An.) and
   *Candida tropicalis* AHU 3410 (Ct.)

Method

Each of the amino compounds of formula (1) was dissolved in ethanol or dimethylsulfoxide (=test solution) in advance. Separately, a brain heart infusion medium (10g, Nissui Seiyaku K.K.), dry bouillon (10 g, Nissui Seiyaku K.K.), yeast extract powder (4 g, Difco Laboratories), and agar (14 g) were added to distilled water (1,000 ml), and heat was applied to dissolve these ingredients. The resultant solution was dispensed in test tubes, 10 ml in each, and the test tubes were pressure-sterilized. Subsequently, each sterilized solution was heated again, and while maintaining its solution state, a test solution or a control liquid (dimethylsulfoxide or ethanol containing no amino compound of formula (1)), each in an amount of 5–200 μl, was added and mixed. The resultant mixture was poured into a plastic petri dish having an inner diameter of 90 mm, and solidified. The solid in the petri dish was divided into 9 sections. A suspension in distilled water of each of the above bacteria (number of bacteria or spores: 106–109/ml) in a volume of 5 μl was inoculated onto each section followed by culturing for 48 hours at 30° C. Growth of the bacteria was visually observed to obtain a minimal concentration (MIC; μg/ml) at which bacteria did not grow.

Results

The results of the above-described antibacterial activity test assessed based on the following five rankings are shown in Table 2.

| Ranking of assessment | Minimal Inhibitory Conc. (MIC) |
|---|---|
| 1 | <3.13 μg/ml |
| 2 | 3.13 μg/ml–12.50 μg/ml |
| 3 | 12.50 μg/ml–50.00 μg/ml |
| 4 | 50.00 μg/ml–100.00 μg/ml |
| 5 | 100.00 μg/ml< |

TABLE 2

| | Sample bacteria | | | | | | |
|---|---|---|---|---|---|---|---|
| | Bs. | Sa. | Se. | Cm. | Pa. | An. | Ct. |
| Compound No. | | | | | | | |
| 1 | 2 | 2 | 2 | 2 | 2 | 2 | 2 |
| 2 | 3 | 3 | 3 | 3 | 3 | 3 | 3 |
| 3 | 2 | 2 | 2 | 2 | 2 | 2 | 2 |
| 4 | 3 | 3 | 3 | 3 | 3 | 3 | 3 |
| 5 | 2 | 3 | 2 | 3 | 2 | 2 | 2 |
| 6 | 2 | 2 | 2 | 2 | 2 | 2 | 2 |
| 7 | 2 | 2 | 2 | 2 | 2 | 3 | 2 |
| 8 | 2 | 2 | 2 | 2 | 2 | 3 | 2 |
| 9 | 2 | 2 | 2 | 2 | 2 | 3 | 2 |
| 10 | 2 | 2 | 2 | 2 | 2 | 2 | 2 |
| 11 | 3 | 3 | 3 | 3 | 3 | 3 | 3 |
| 12 | 3 | 3 | 3 | 3 | 3 | 3 | 3 |
| 13 | 2 | 2 | 2 | 2 | 2 | 2 | 2 |
| 14 | 2 | 2 | 2 | 2 | 2 | 3 | 2 |
| 15 (Control compound) | 2 | 2 | 2 | 2 | 2 | 2 | 2 |
| Butyl paraben | 4 | 5 | 5 | 5 | 5 | 5 | N.T. |

N.T.: Not Tested

Test Example 3 (safety test)

Method

Five (5) or ten (10) Hartley guinea pigs (female, body weight: 350–400 g) are used. A 1 wt % solution of each test compound in acetone was prepared, and the solution was tested with respect to its sensitizing potential, primary stimulation to the skin, and photo-toxicity.

As test compounds, three compounds, i.e., compound Nos. 1, 10, and 14 in Table 1, were used.

The sensitization test was performed in accordance with the maximization method proposed by Magnusson [Magnusson, B and Kligman, A.M.,; "The identification of contact allergens by animal assay. The guinea pig maximization test" (J. Inv. Derm., 52, p268–276 (1969))]. The induction of sensitization was performed at a concentration of 10 wt %.

The positive control compound used for the photo-toxicity was an ethanol solution containing 100 ppm of 8-methoxypsoralen (product of Aldrich). The light source used was FL-40S.BLB (300–400 nm; manufactured by Toshiba).

Results

Judgments were visually made, and the results are shown in Table 3.

TABLE 3

| Test Compounds | No. of animals with positive results/ No. of tested animals | | |
|---|---|---|---|
| (No.) | Sensitization | Primary stimulation | Photo-toxicity |
| 1 | 0/10 | 0/5 | 0/5 |
| 10 | 0/10 | 0/5 | 0/5 |
| 14 | 0/10 | 0/5 | 0/5 |

As is apparent from Table 3, none of the test compounds exhibited any evidence of sensitization, primary stimulation, or photo-toxicity.

As described hereinbefore, amino compounds of formula (1) exhibit excellent antibacterial effects and fungicidal effects. They may be used singly to obtain their antibacterial and fungicidal effects. When they are applied to a variety of articles used in industry, commodities, etc., enhanced antibacterial effects and fungicidal effects are obtained.

What is claimed is:

1. A method for imparting antibacterial and fungicidal properties to an article of manufacture or a composition which may allow propagation of bacteria, fungi or both, comprising physically contacting the article of manufacture or composition with an antibacterially or fungicidally effective amount of an amino compound of formula (1) or a salt thereof:

wherein

φ represents (1) a phenyl group, (2) a substituted phenyl group, wherein the number of substituents is 1 from 5 inclusive, and the substituents, which may be identical to or different from one another, are selected from the group consisting of a hydroxyl group, halogen atoms, lower alkoxyl groups, trifluoromethyl group, an amino group, and a methylenedioxy group, or (3) an imidazolyl group;

$R^1$ represents a hydrogen atom or a lower alkyl group; and $R^2$ represents a C6–12 alkyl group.

2. The method as defined in claim 1, wherein φ is a substituted phenyl group.

3. The method as defined in claim 1, wherein φ is a methylenedioxy-substituted phenyl group.

4. The method of claim 1 wherein φ represents a phenyl group.

5. The method of claim 1, wherein $R^1$ represents a hydrogen atom.

6. The method of claim 1, wherein $R^1$ represents a C1–C4 alkyl group.

7. The method according to claim 1, wherein φ is a 3,4-methylenedioxyphenyl group, $R^1$ is a hydrogen atom and $R^2$ is a $C_{12}H_{25}$ group.

8. The method as defined in claim 1, wherein the article of manufacture or composition comprises 0.001 to 2% by weight after being physically contacted with the amino compound of formula (1) or a salt thereof.

9. The method as defined in claim 1 wherein the article of manufacture or composition is selected from the group consisting of cosmetics, toiletry goods, sterilizing agents, deodorants, detergents, paints, wall papers, adhesives, wall boards, tiles, cement, concrete, molded resins, fibers and porcelains.

* * * * *